(12) United States Patent
DeVita

(10) Patent No.: US 10,780,142 B2
(45) Date of Patent: Sep. 22, 2020

(54) ALOE-HYPLEX TOPICAL FORMULATION AND A METHOD OF PREPARATION

(71) Applicant: Cherylanne DeVita, Glendale, AZ (US)

(72) Inventor: Cherylanne DeVita, Glendale, AZ (US)

( * ) Notice: Subject to any disclaimer, the term of this patent is extended or adjusted under 35 U.S.C. 154(b) by 0 days.

(21) Appl. No.: 16/815,603

(22) Filed: Mar. 11, 2020

(65) Prior Publication Data

US 2020/0206294 A1    Jul. 2, 2020

(51) Int. Cl.
| | | |
|---|---|---|
| *A61K 36/00* | (2006.01) |
| *A61K 36/886* | (2006.01) |
| *A61K 36/82* | (2006.01) |
| *A61K 9/06* | (2006.01) |
| *A61K 47/10* | (2017.01) |
| *A61K 47/36* | (2006.01) |
| *A61K 9/00* | (2006.01) |

(52) U.S. Cl.
CPC .......... *A61K 36/886* (2013.01); *A61K 9/0014* (2013.01); *A61K 9/06* (2013.01); *A61K 36/82* (2013.01); *A61K 47/10* (2013.01); *A61K 47/36* (2013.01)

(58) Field of Classification Search
CPC ...................................................... A61K 36/00
USPC .......................................................... 424/725
See application file for complete search history.

(56) References Cited

FOREIGN PATENT DOCUMENTS

KR        1515865        *   5/2015

* cited by examiner

*Primary Examiner* — Michael V Meller
(74) *Attorney, Agent, or Firm* — Barry Choobin; Patent 360

(57) ABSTRACT

The present invention relates to aloe-hyplex topical formulation and a method of preparation for multilayer skin delivery of active ingredients to provide skin rejuvenating effect. The aloe-hyplex formulation comprises of: a) aloe vera leaf extract in the range of 5-15% by wt., b) at least one anti-inflammatory agent in the range of 5-15% by wt., c) sodium hyaluronate in the range of 0.001-0.1% by wt., d) glycerin in the range of 50-85% by wt., and e) water in the range of 0.5-5% by wt. The method of preparation of the formulation comprises of mixing and stirring the aloe vera extract, anti-inflammatory agent, sodium hyaluronate, glycerin and water to obtain a homogenous aloe-hyplex formulation.

1 Claim, No Drawings

ALOE-HYPLEX TOPICAL FORMULATION AND A METHOD OF PREPARATION

CROSS REFERENCE

This application claims the benefit of U.S. Provisional Application No. 62/791,579, entitled "Aloe-Hyplex" filed Jan. 11, 2019, the contents of which are incorporated herein by reference in their entireties and for all purposes.

FIELD OF THE INVENTION

The present invention relates to topical skin rejuvenating formulations and method of preparation. More particularly, the present invention relates to "aloe-hyplex" topical formulation and a method of preparation, for multilayer skin penetration and delivery of active pharmaceutical agents thereby providing an overall skin rejuvenating effect.

BACKGROUND OF THE INVENTION

Human skin is the outermost covering of our body and is often exposed to harsh external conditions. Such exposure over time leads to anatomical degradation of the skin. The most affected areas of skin where the signs of degradation are most pronounced are face and around the eyes. The symptoms of skin degradation are observed as wrinkles, fine lines, dark circles under eyes, age blemishes, leathery skin texture, dryness, roughness, and premalignant growths. Although, our skin possesses a natural ability to combat such damage by repairing itself. But with aging, the natural ability of the skin to repair itself decreases.

Maintaining a healthy skin is as important as maintaining the internal health of our body. Therefore, efforts have been made since long to treat human skin to counter the above symptoms of skin degradation and rejuvenate the layers of skin.

The early work in skin rejuvenation is focused on the use of vitamin A or retinol as a therapeutic agent, where vitamin A is administered internally. Later topical application of vitamin A in its acid form (retinoic acid) has shown promising results in retarding the symptoms of ageing. However, the topical use of retinoic acid has its demerits like painful and unpleasant peeling of the skin. Due to this drawback, the use of vitamin A in its various forms has limited applicability.

Further scientific research on anti-aging and skin rejuvenation has focused mainly on selective natural products due to their better acceptability towards human skin. The prior art, U.S. Pat. No. 6,146,650 describes the use of liposomes to deliver collagen, avocado oil, aloe and vital nutrients such as Vitamins A, C, D and E to the skin.

U.S. Pat. No. 7,608,642 describes about pharmaceutical compositions and methods for managing wound and skin care that particularly employs compounds that promote skin cell renewal, wound healing, proliferation of fibroblasts and/or keratinocytes, and production of collagen in dermal layers.

One of the compounds which are currently used in many commercially available skin rejuvenating and anti-aging products is hyaluronic acid. Hyaluronic acid possesses great water retention capacity and can hold up to 1000 times its weight in water. But the high molecular weight of the hyaluronic acid polymer does not allow it to penetrate the epidermal layer of skin and therefore cannot reach the deeper layers.

Hyaluronic acid is an internal supplement and is recently used topically on the skin. In most skin rejuvenating products where hyaluronic acid is used for topical application, only a single sized molecule of high molecular weight hyaluronic acid is used which penetrates only the top layer (epidermis) of skin. This drawback is countered by using sodium salt of hyaluronic acid which is a low molecular weight derivative of hyaluronic acid.

Cosmetic compositions containing low molecular weight sodium salt of hyaluronic acid are known. The European patent EP 1.689.356 describes about a topical composition containing low molecular weight (50-75 kDa) sodium hyaluronate and retinal. But such compositions do not describe about the deep layer delivery of natural anti-inflammatory agents.

Aloe vera or *Aloe barbadensis* Miller leaf gel is rich in polysaccharides and anti-inflammatory compounds which are responsible for most of the therapeutic properties of aloe vera. The high polysaccharide aloe vera extract can penetrate to the deeper layers of the skin (dermis) and acts as a potential carrier for other active ingredients.

Multilayer skin penetration of hyaluronic acid can be achieved by using a source of sodium hyaluronate having a mixture of both high and low molecular weight hyaluronic acid.

To overcome the drawbacks of the prior arts, there is a need to develop a topical formulation with multilayer skin penetration and having a synergistic combination of natural active agents such as aloe vera and a source of high-low molecular weight sodium hyaluronate (aloe-hyplex), and a method of preparation to provide an overall skin rejuvenating effect.

OBJECTS OF THE INVENTION

The principal object of the present invention is to overcome the disadvantages of the prior art.

An object of the present invention is to provide aloe-hyplex topical formulation and a method of preparation for rejuvenating skin.

Another object of the present invention is to provide a topical formulation for multilayer skin delivery of active pharmaceutical agents.

Another object of the present invention is to provide a formulation based on hyaluronic acid enrichment by utilizing a source of high-low molecular weight hyaluronic acid.

Yet another object of the present invention is to provide a formulation to enhance water retention or moisture content of the skin.

The foregoing and other objects of the present invention will become readily apparent upon further review of the following detailed description of the preferred embodiment.

SUMMARY OF THE INVENTION

The present invention relates to aloe-hyplex topical formulation and a method of preparation for multilayer skin delivery of active agents to provide an overall skin rejuvenating effect by enhancing moisture retention of skin.

According to an embodiment of the present invention, the aloe-hyplex topical formulation essentially comprises of: a) aloe vera leaf extract in the range of 5-15% by wt., b) an anti-inflammatory agent in the range of 5-15% by wt., c) sodium hyaluronate in the range of 0.001-0.1% by wt., d) glycerin in the range of 50-85% by wt., and e) water in the range of 0.5-5% by wt.

According to another embodiment of the present invention, a method of preparation of the aloe-hyplex formulation comprises the steps of mixing and stirring the aloe vera extract, anti-inflammatory agent, sodium hyaluronate, glycerin and water to obtain a homogenous aloe-hyplex topical formulation.

While the invention has been described and shown with particular reference to the preferred embodiment, it will be apparent that variations might be possible that would fall within the scope of the present invention.

DETAILED DESCRIPTION OF THE INVENTION

As required, detailed embodiments of the present disclosure are disclosed herein; however, it is to be understood that the disclosed embodiments are merely exemplary of the disclosure which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Various other objects, advantages, and features of the disclosure will become more readily apparent to those skilled in the art from the following detailed description when read in conjunction with the accompanying drawing.

In any embodiment described herein, the open-ended terms "comprising," "comprises," and the like (which are synonymous with "including," "having" and "characterized by") may be replaced by the respective partially closed phrases "consisting essentially of," consists essentially of," and the like or the respective closed phrases "consisting of," "consists of," the like.

As used herein, the singular forms "a," "an," and "the" designate both the singular and the plural, unless expressly stated to designate the singular only.

As used herein, the term, "sodium hyaluronate" refers to a sodium salt of hyaluronic acid. Sodium hyaluronate molecule holds up to 1000 times its weight in water thereby responsible for its hydrating effect. Sodium hyaluronate when applied to skin greatly enhances its water retention ability and acts as a skin revitalizer.

As used herein, the term, "aloe vera" refers to *Aloe barbadensis* Miller, a perennial plant having succulent leaves. Many of the medicinal properties of aloe vera are attributed to the high polysaccharide content of the leaf gel. The aloe vera leaf extract is prepared from the aloe vera leaf gel and provides skin rejuvenating and soothing effects.

As used herein, the term, "aloe-hyplex" refers to a synergistic combination of aloe vera extract and hyaluronic acid, which when applied topically provides skin rejuvenating effect.

As used herein, the term, "*Camellia sinensis*" refers to an evergreen shrub also known as tea tree. The leaves and leaf buds of this shrub are used to produce yellow, green, black, oolong and fermented teas. The unprocessed young leaves and leaf buds are used to obtain green tea. Green tea extract is rich in anti-inflammatory and antioxidant properties.

The present invention relates to aloe-hyplex topical formulation and a method of preparation for multilayer skin penetration and delivery of active pharmaceutical agents to enhance skin hydration and provide skin revitalizing effect.

The aloe-hyplex topical formulation comprises of: a) 5-15% by wt. of aloe vera leaf extract, b) 5-15% by wt. of an anti-inflammatory agent, c) 0.001-0.1% by wt. of sodium hyaluronate, d) 50-85% by wt. of glycerin, and e) 0.5-5% by wt. of water.

Aloe vera leaf extract is obtained from the leaf gel of *Aloe barbadensis*. The aloe vera leaf extract acts a carrier for delivering active pharmaceutical agent to the deeper layers of the skin as well as a hydrating agent. The quantity of aloe vera leaf extract in the aloe-hyplex formulation is preferably 10% by weight.

The anti-inflammatory agent in the aloe-hyplex formulation is selected from a group consisting of *Camellia sinensis* leaf extract, grape seed extract and liquorice extract. The preferable anti-inflammatory agent in the aloe-hyplex formulation is *Camellia sinensis* or green tea leaf extract. The amount of green tea leaf extract in the formulation is preferably 8.30% by weight.

Sodium hyaluronate is a sodium salt derivative of hyaluronic acid and has lower molecular weight than hyaluronic acid. The source of sodium hyaluronate in the formulation comprises a mixture of both high and low molecular weight hyaluronic acid which enables penetration through the top (dermis) and the inner layer (epidermis) of skin. The low molecular weight sodium hyaluronate penetrates into deeper layers of the skin and retains moisture to provide a wrinkle free and plump skin. The molecular weight of sodium hyaluronate in the formulation ranges from 5 kDa-50 kDa. The amount of sodium hyaluronate in the aloe-hyplex formulation is preferably 0.01% by weight.

Glycerin acts as a humectant and hydrates the skin. The amount of glycerin in the formulation is preferably 80% by weight.

The amount of water in the formulation is preferably 1.69% by weight.

The method of preparation of the aloe-hyplex formulation comprises of the following steps: i) mixing the aloe vera leaf extract, *Camellia sinensis* leaf extract, sodium hyaluronate, glycerin and water to obtain a homogenous mixture, and ii) stirring the homogenous mixture for about 20 minutes to obtain the aloe-hyplex topical formulation.

The aloe-hyplex topical formulation can be formulated in a cosmetically acceptable base of gel, cream, lotion or ointment. The aloe-hyplex formulation is homogenous in texture. The topical formulation is hypoallergenic.

Table 1 shows the various ingredients and their quantity in the aloe-hyplex formulation.

TABLE 1

| *Aloe*-Hyplex formulation | |
| --- | --- |
| Ingredients | Quantity (% by wt.) |
| *Aloe vera* leaf extract | 10 |
| *Camellia sinensis* leaf extract | 8.30 |
| Sodium hyaluronate | 0.01 |
| Glycerin | 80 |
| Water | 1.69 |

The low molecular weight sodium hyaluronate (5-50 kDa) penetrates the upper layer or epidermis layer of the skin. The addition of aloe vera and green tea leaf extract in the aloe-hyplex formulation enhances skin penetration thereby allows the sodium hyaluronate molecules to reach into the deeper dermis layer of the skin. This results in enhanced water retention in the deeper layers of the skin causing a plumper skin with reduced appearance of fine lines and wrinkles. This property makes the aloe-hyplex formulation effective as a skin revitalizer and an anti-ageing cosmetic.

While the disclosure has been presented with respect to certain specific embodiments, it will be appreciated that many modifications and changes may be made by those skilled in the art without departing from the spirit and scope of the disclosure.

I claim:

1. A composition which provides an overall human skin rejuvenating effect by enhancing moisture retention of the human's skin consisting essentially of:
   a) 5-15% by wt. of an aloe vera leaf extract;
   b) 5-15% by wt. of a *Camellia sinensis* extract;
   c) 0.001-0.1% by wt. of sodium hyaluronate;
   d) 50-85% by wt. of glycerin; and
   e) 0.5-5% by wt. of water.

* * * * *